United States Patent [19]

Rosen

[11] 4,151,196

[45] Apr. 24, 1979

[54] CYANO-ENOL ETHERS

[75] Inventor: Perry Rosen, North Caldwell, N.J.

[73] Assignee: Hoffmann-La Roche Inc., Nutley, N.J.

[21] Appl. No.: 921,646

[22] Filed: Jul. 3, 1978

Related U.S. Application Data

[62] Division of Ser. No. 770,322, Feb. 18, 1977, abandoned, which is a division of Ser. No. 590,755, Jun. 26, 1975, Pat. No. 4,033,962.

[51] Int. Cl.² .......................................... C07C 121/75
[52] U.S. Cl. ................................................ 260/465 F
[58] Field of Search ..................................... 260/465 F

[56] References Cited

U.S. PATENT DOCUMENTS

| | | | |
|---|---|---|---|
| 2,658,897 | 11/1953 | Hitchings et al. | 260/256.4 N |
| 3,341,541 | 9/1967 | Hoffer | 260/256.4 N |
| 3,855,265 | 12/1974 | Cresswell et al. | 260/465 E |

*Primary Examiner*—Dolph H. Torrence
*Attorney, Agent, or Firm*—Jon S. Saxe; George M. Gould; William G. Isgro

[57] ABSTRACT

The present invention relates to a new synthesis for the preparation of 5-(substituted benzyl)-2,4-diamino-pyrimidines, including new pyrimidine derivatives. More particularly, a new synthesis of ormetoprin, diaveridine and related compounds, including novel derivatives, is disclosed. The synthesis involves the condensation of a substituted benzene and an acrylonitrile derivative to directly give enol ether intermediates, which upon subsequent reaction by known techniques with guanidine, provides the desired 5-(substituted benzyl)-2,4-diamino-pyrimidines, including novel compounds. The pyrimidine end products are useful as potentiators of sulfonamides and as antibacterial agents.

2 Claims, No Drawings

CYANO-ENOL ETHERS

This is a division of application Ser. No. 770,322 filed Feb. 18, 1977, and now abandoned which is a division of application Ser. No. 590,755, filed June 26, 1975, now U.S. Pat. No. 4,033,962, patented July 5, 1977.

BRIEF SUMMARY OF THE INVENTION

The invention relates to a process for preparing pyrimidine compounds. More particularly, the invention relates to a process for the preparation of pyrimidines of the formula

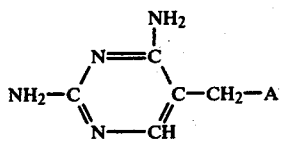

wherein A is aryl, for example, a radical of the formula

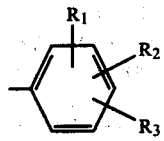

wherein $R_1$, $R_2$ and $R_3$ are hydrogen, lower alkyl, lower alkoxy or non-conjugated lower alkenyl, by reacting the correspondingly substituted benzene and an acrylonitrile derivative in the presence of an acid catalyst, with or without solvent, to obtain the corresponding enol ether which is thereafter reacted with guanidine to yield the desired 2,4-diamino-pyrimidine.

In another aspect, the invention relates to pyrimidines of the formula

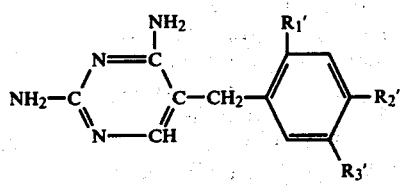

wherein $R_1'$ is hydrogen, lower alkyl, lower alkoxy or lower alkenyl, and $R_2'$ and $R_3'$ are lower alkoxy or lower alkenyl, provided that at least one of $R_1'$, $R_2'$ and $R_3'$ is lower alkenyl, and pharmaceutically acceptable acid addition salts thereof.

In yet another aspect, the invention relates to compounds of the formula

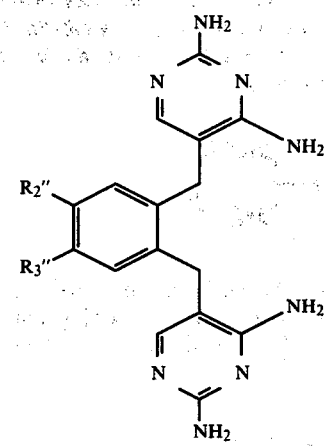

wherein $R_2''$ and $R_3''$ are, independently, lower alkoxy.

In a still further aspect, the invention relates to intermediates of the formulas

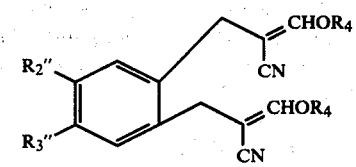

wherein $R_2''$ and $R_3''$ are as hereinbefore described, and $R_4$ is lower alkyl, and

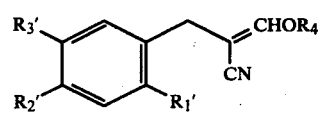

wherein $R_1'$ is hydrogen, lower alkyl, lower alkoxy or lower alkenyl, and $R_2'$ and $R_3'$ are lower alkoxy or lower alkenyl, provided that at least one of $R_1'$, $R_2'$ and $R_3'$ is lower alkenyl, and $R_4$ is lower alkyl.

DETAILED DESCRIPTION OF THE INVENTION

The term "lower alkyl" as used herein is intended to denote straight or branched chain alkyl groups having 1–7 carbon atoms, most preferably 1–4 carbon atoms, e.g., methyl, ethyl, propyl, isopropyl, butyl, hexyl, heptyl, and the like. The expression "lower alkoxy" denotes a straight or branched chain alkoxy group having 1–7, most preferably 1–4 carbon atoms, e.g., methoxy, ethoxy, propoxy, isopropoxy, butoxy, hexoxy, heptoxy, and the like. The term "non-conjugated lower alkenyl" denotes an unsaturated hydrocarbon group having 3–7 carbon atoms such as 2-propenyl, 2-butenyl, 2-pentenyl, and the like. The term "lower alkenyl" denotes an unsaturated hydrocarbon group having 3–7 carbon atoms such as 1-propenyl, 2-propenyl, and the like. The term "aryl" denotes preferably phenyl or phenyl bearing, independently, 1 to 3 substituents from the group consisting of lower alkyl, lower alkoxy, lower alkenyl or halogen. Exemplary of such groups are 2-methyl-4,5-dimethoxyphenyl, 3,4-dimethoxyphenyl, 2-(2-propenyl)-4,5-dimethoxybenzyl or the like. The term "halogen" denotes bromine, chlorine, fluorine and iodine; preferably, chlorine or bromine.

The process of the invention comprises reacting an aromatic benzene derivative which yields a residue referred to as A, for example, an aromatic benzene derivative of the formula

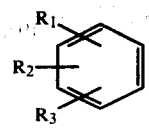   IV wherein $R_1$, $R_2$ and $R_3$, independently, are hydrogen, lower alkyl, lower alkoxy or non-conjugated lower alkenyl, preferably a benzene derivative of the formula

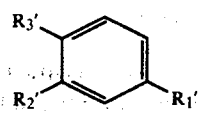   IVa wherein $R_1'$ is hydrogen, lower alkyl, lower alkoxy or non-conjugated lower alkenyl, and $R_2'$ and $R_3'$, independently, are lower alkoxy or non-conjugated alkenyl, with an acrylonitrile selected from the group consisting of a compound of the formula

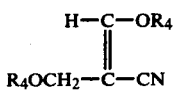   V and a compound of the formula

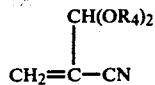   VI wherein $R_4$ is, independently, lower alkyl, to thereby obtain the corresponding enol ether, for example, an enol ether of the formula

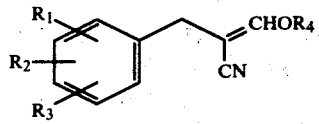   VII wherein $R_1$, $R_2$, $R_3$ and $R_4$ are as described above, and subsequently treating the so-obtained enol ether with guanidine to obtain the corresponding pyrimidine, for example, a pyrimidine of the formula

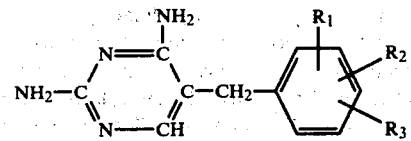   I wherein $R_1$, $R_2$ and $R_3$ are as previously described.

Of the compounds of formula VII, those which have the formula

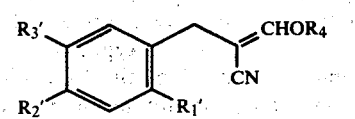   VIIa wherein $R_1'$ is hydrogen, lower alkyl, lower alkoxy or lower alkenyl, and $R_2'$ and $R_3'$ are lower alkoxy or lower alkenyl, provided that at least one of $R_1'$, $R_2'$ and $R_3'$ is lower alkenyl, and $R_4$ is lower alkyl, are novel compounds.

In the reaction of the aromatic benzene derivatives with an acrylonitrile of formula V or VI, in addition to the enol ether, for example, the enol ether of formula VII, there may also be produced varying amounts of the corresponding acetal of the formula

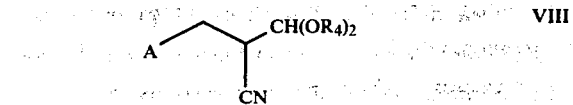   VIII preferably an acetal of the formula

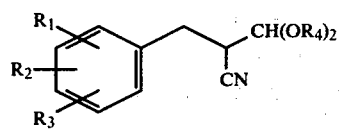   VIIIa wherein $R_1$, $R_2$, $R_3$ and $R_4$ are as previously described.

It has been found that p-toluenesulfonic acid gives the highest proportion of acetal. If a mixture of the enol ether and acetal is formed in the reaction, the acetal need not be removed from the reaction mixture nor need the enol ether be separated from the reaction mixture. The subsequent reaction with guanidine can be effected with the mixture to yield the desired pyrimidine.

Of the compounds of formula VIIIa, those which have the formula

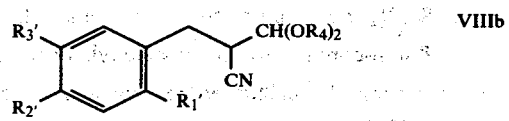   VIIIb wherein $R_1'$ is hydrogen, lower alkyl, lower alkoxy or lower alkenyl, and $R_2'$ and $R_3'$ are lower alkoxy or lower alkenyl, provided at least one of $R_1'$, $R_2'$ and $R_3'$ is lower alkenyl and $R_4$ is lower alkyl, are novel compounds.

The reaction of the aromatic benzene derivative, for example, a compound of formula IV or IVa with a compound of formula V or of formula VI is carried out in the presence of an acid catalyst.

Suitably, the reaction is effected in the presence of an inert organic solvent type normally employed in a Friedel-Crafts reaction, for example, methylene chloride. Exemplary of the acid catalysts are, for example, Lewis acids, such as boron trifluoride, boron trifluoride etherate, aluminum chloride, ferric chloride, zinc chloride, titanium tetrachloride, or the like; methanesulfonic acid, p-toluene-sulfonic acid; benzene-toluenesulfonic acid; or the like.

The amount of catalyst to be used is not critical, but it is preferred to use from about 1 to about 10% by mole weight of catalyst based upon the weight of benzene derivative.

The aromatic benzene derivatives, for example, the compounds of formulas IV and IVa are known compounds or can be prepared according to known procedures. Exemplary of such compounds are 3,4-dimethoxy-toluene, toluene, veratrole, methyleugenol, benzene, or the like.

The compounds of formulas V and VI are known compounds or can be prepared according to known procedures. Exemplary of such compounds are α-methoxy-methylene-β-methoxypropionitrile, 2-dimethoxy-methylacrylonitrile, or the like.

The compound of formula VI has been found to be more reactive than the compound of formula V. It has been postulated that during the reaction of a compound of formula V with a compound of formula IV, a compound of formula VI results. The compound of formula VI then partakes in the reaction to the desired enol ether, for example, a compound of formula VII.

When a compound of formula VI is a starting material, the propensity of the Lewis acid catalyst to accept electron pairs need not be of as high an order as the Lewis acid required when a compound of formula V is a starting material. Thus, with a compound of formula VI, catalysts such as zinc chloride may be utilized, whereas with a compound of formula V, stronger electron pair accepting Lewis acid catalysts must be utilized, such as boron trifluoride etherate, aluminum trichloride, para-toluenesulfonic acid, or the like. Those skilled in the art with the above description, can readily recognize the Lewis acids suitable as catalyst in the process described herein.

It has been observed that under the reaction conditions employed in effecting the preparation of the enol ether, for example, a compound of formula VII, that it need not be isolated from the reaction mixture, but can be reacted in situ with guanidine, that is, the guanidine can be directly added to the reaction vessel in which the enol ether, for example, a compound of formula VII is prepared via the reaction of an aromatic benzene derivative, for example, a compound of formula IV with either a compound of formula V or of formula VI without isolating the so-obtained enol ether, for example, a compound of formula VII. Thus, by the process defined herein, there is provided to the art, a simple "one-pot" procedure which avoids the use of duplicate equipment, isolation procedures and extensive time delays which, when avoided, provide the art with a highly desirable process from a commercial point of view.

Furthermore, the condensation reaction can be conducted with or without a solvent. Exemplary of such solvents are halogenated hydrocarbons such as methylene chloride or the like; and other solvents commonly used in a Friedel-Crafts reaction. The conversion of the enol ether, for example, a compound of formula VII to the compounds of formula I can be carried out with a solvent such as dimethylformamide, hexamethylphosphoramide; alkanols such as t-butanol; or the like.

While the reaction temperature is not a critical aspect of the process herein disclosed, it is preferred to carry out the reaction at a temperature in the range of from about 0° to about 45°, most preferably at about room temperature.

The process described herein is particularly desirable because is provides the art with a new and novel approach to the pharmaceutically valuable compounds of formula I in high yields and good quality.

The compounds of formula I form acid addition salts and such salts are also within the scope of this invention. Thus, the compounds of formula I form pharmaceutically acceptable addition salts with, for example, both pharmaceutically acceptable organic and inorganic acids, such as acetic acid, succinic acid, formic acid, methanesulfonic acid, p-toluenesulfonic acid, hydrochloric acid, nitric acid, phosphoric acid, sulfuric acid, lactic acid, and the like.

The compounds of formula I and Ia are useful in combination with one or more sulfa drugs, such as, for example, $N^1$-(3,4-dimethyl-5-isoxazolyl)-sulfanilamide, 5-methyl-3-sulfanilamido-isoxazole, $N^1$-(2,6-dimethoxy-4-pyrimidinyl)-sulfanilamide, $N^4$-ethoxyacetyl-$N^1$-(5-methyl-3-isoxazolyl)-sulfanilamide, $N^1$-(4,5-dimethyl-3-isoxazolyl)sulfanilamide, $N^1$-(5,6-dimethoxy-4-pyrimidinyl)-sulfanilamide, and the like, as antibacterial agents. The addition of a compound of formula I or Ia to one of the above-mentioned sulfonamides results in a marked potentiation of the antibacterial activity of the sulfonamide. Thus, the compounds of formula I and Ia are useful as potentiators of sulfonamides. The combination of a compound of formula I or Ia and a sulfonamide is prepared simply by admixture, which can ultimately be embodied into a suitable oral dosage form, as hereinafter described.

The ratios in which a therapeutically active compound of formula Ia and a sulfonamide are utilized can be varied within wide limits. For example, the combination can contain from about 1 to about 40 parts, preferably from about 1 to about 20 parts, of sulfonamide or an equivalent amount of salt thereof to one part of a compound of formula Ia or equivalent amount of salt thereof.

The products of the invention can be incorporated into standard pharmaceutical dosage forms, for example, they are useful for oral or parenteral application with the usual pharmaceutical adjuvant material, for example, organic or inorganic inert carrier materials such as water, gelatin, lactose, starch, magnesium stearate, talc, vegetable oils, gums, polyalkyleneglycols, and the like. The pharmaceutical preparations can be employed in a solid form, for example, as tablets, troches, suppositories, capsules or in liquid form, for example, as solutions, suspensions or emulsions. The pharmaceutical adjuvant material can be added and can include preservatives, stabilizers, wetting or emulsifying agents, salts to change the osmotic pressure or to act as buffers. They can also contain other therapeutically active materials. The combination of a compound of formula Ia and a sulfonamide can be administered in unit dosage forms which contain 500 mg. of sulfonamide or an equivalent amount of a salt thereof and from about 12.5 mg. to about 100 mg. of a compound of formula Ia or an equivalent amount of a salt thereof. However, it is also within the scope of the invention to utilize a unit dosage form which will contain from about 250 mg. to about 750 mg. of sulfonamide or equivalent amount of a salt thereof and from about 5 mg. to about 150 mg. of a compound of formula Ia or equivalent amount of a salt thereof.

The frequency with which any such unit dosage will be administered to a warm-blooded animal will vary, depending upon the quantity of medicament present therein and the needs and requirements of the warm-blooded animal.

The sulfonamides hereinbefore described form salts with pharmaceutically acceptable bases, for example, they form salts with alkali metal bases, such as, for example, sodium hydroxide, potassium hydroxide or the like.

The following Examples further illustrate the invention. All temperatures are stated in degrees Centigrade, unless otherwise mentioned.

EXAMPLE 1

Preparation of 1,2-dimethoxy-4-methyl-5-(2-cyano-3-methoxy-2-propenyl)benzene

To a solution of 10 g. of 3,4-dimethoxytoluene and 10.9 g. of α-methoxy-methylene-β-methoxypropionitrile dissolved in 50 ml. of dry methylene chloride was added in small portions at 0° C., 8.8 g. of aluminum chloride. After the addition was complete, the mixture was stirred for 5 minutes at 0°, after which time the ice bath was removed and the reaction mixture stirred for an additional 3.5 hours. The reaction was then treated with ether and the mixture poured into 200 ml. of ice water. The organic layer was separated and the aqueous solution extracted with 2×200 ml. of methylene chloride. The organic layers were combined, washed with a 5% sodium bicarbonate solution and dried (MgSO$_4$). The solvent was removed under reduced pressure and the residue distilled through an oil jacketed flask to give 13.6 g. (84%) of 1,2-dimethoxy-4-methyl-5-(2-cyano-3-methoxy-2-propenyl)benzene, b.p. 180–185/0.05 mm.

EXAMPLE 2

Preparation of 2,4-diamino-5-(4,5-dimethoxy-2-methylbenzyl)pyrimidine

To a solution of 10 g. of 3,4-dimethoxytoluene and 9.6 g. of 2-dimethoxymethylacrylonitrile in 200 ml. of dry methylene chloride was added dropwise at 0°, 2.3 ml. (0.0197 mole) of stannic chloride. The reaction mixture was stirred for 6 hours at 20°–25°, diluted with 500 ml. of ether, and the resulting solution washed with a 5% sodium bicarbonate solution until the aqueous layer remained basic. The combined aqueous washings were backwashed with ether and the organic layers were then combined and dried (MgSO$_4$). The solvent was then removed under reduced pressure leaving an off-white residue of crude 1,2-dimethoxy-4-methyl-5-(2-cyano-3-methoxy-2-propenyl)benzene.

A fresh solution of sodium methoxide in methanol was prepared by reacting 3.04 g. (0.132 mole) of sodium with 40 ml. of dry methanol. To this solution was then added a solution of the crude enol ether (16.5 g.) dissolved in 50 ml. of dry dimethylformamide. Solid guanidine hydrochloride (13.1 g., 0.132 mole) was then added and the resulting mixture stirred and slowly heated to 145° C. The refluxing methanol was removed by means of a Dean-Stark trap and the reaction was stirred and heated at 145° for an additional 2 hours (reaction was monitored by thin layer chromatography). The heat was removed and the reaction stirred overnight, cooled to 0° C. and filtered. The residue was washed with cold dimethylformamide, water and dried at 100° under vacuum to give 15.5 g. (86%) of 2,4-diamino-5-(4,5-dimethoxy-2-methylbenzyl)pyrimidine, as a white crystalline solid, m.p. 232°–234° C.

EXAMPLE 3

Preparation of 2,4-diamino-5-(4,5-dimethoxy-2-methylbenzyl)pyrimidine ("One Pot Procedure")

To a mixture of 10.4 g. of 3,4-dimethoxytoluene and 10 g. of α-methoxy-methylene-β-methoxypropionitrile was added 2 ml. of boron trifluoride etherate. The mixture was stirred and heated at 50° for 18 hours. The reaction was then cooled and 17.3 g. of guanidine hydrochloride and 50 ml. of dry dimethylformamide added. After stirring for 5 minutes, a fresh solution of methanolic sodium methoxide (4 g. sodium dissolved in 40 ml. of dry methanol) was added under argon. The reaction mixture was then slowly heated (oil bath) to 140° while removing the methanolic distillate via a Dean-Stark apparatus. After removal of the methanol, the reaction was heated and stirred at 140° for an additional hour. The heat was then removed and the reaction stirred for 18 hours. The mixture was then cooled to 0° and filtered. The residue was washed with a small amount of cold dimethylformamide (20 ml.) followed by ice water and air dried. The slightly yellow product was then dissolved in one liter of a solution made up of 50 parts trichloromethane, 25 parts methanol and 25 parts ethyl acetate, charcoaled and filtered. The solvent was then removed under reduced pressure to give 14.7 g. (78%) of white crystalline 2,4-diamino-5-(4,5-dimethoxy-2-methylbenzyl)-pyrimidine, m.p. 228°–231°.

EXAMPLE 4

Preparation of 3-methoxy-2-(veratryl)acrylonitrile

To a solution of 27.2 g. (0.197 mole) of veratrole and 10 g. of 2-dimethoxymethacrylonitrile in 100 ml. of dry methylene chloride was added dropwise 2.75 ml. of stannic chloride. The reaction mixture was then stirred at 20°–25° for 3.5 hours. The mixture was diluted with 200 ml. of ether and then washed with 3×100 ml. of a 5% sodium bicarbonate solution. The water washings were extracted with ether and the organic layers combined and dried (MgSO$_4$). The solvent was then removed under reduced pressure and the residue distilled to give 17 g. of veratrole, b.p. 60°–70°/5 mm. and 13.9 g. of 3-methoxy-2-(veratryl)acrylonitrile, b.p. 177°–180°/0.2 mm. A small sample of distilled product was cooled and triturated with ether to give a solid, m.p. 64°–65°.

EXAMPLE 5

Preparation of 1,2-dimethoxy-4,5-bis-(2-cyano-3-methoxy-2-propenyl)-benzene

To a solution of 15 g. of veratrole and 31.8 g. of 2-dimethoxymethylacrylonitrile in 150 ml. of dry methylene chloride was added 6.35 ml. of stannic chloride. The mixture was stirred at room temperature for 48 hours, after which time an additional 3.18 ml. of stannic chloride was added. After the reaction was stirred an additional 4 hours, 100 ml. of methylene chloride and 200 ml. of ethyl acetate were added. The mixture was then washed with a 5% sodium bicarbonate solution (until basic) and the aqueous phase back-washed with ethyl acetate. The organic layers were combined and dried (MgSO$_4$). The solvent was removed under vacuum and the residue triturated with ether to give 31.7 g. (88.8%) of 1,2-dimethoxy-4,5-bis-(2-cyano-3-methoxy-2-propenyl)benzene, m.p. 124°–125°.

EXAMPLE 6

Preparation of 1,2-dimethoxy-4,5-bis-(2,4-diamino-5-pyrimidinylmethyl)benzene

A mixture of 10 g. (0.0305 mole) of 1,2-dimethoxy-4,5-bis-(2-cyano-3-methoxy-2-propenyl)benzene and 6.6 g. of guanidine carbonate in 30 ml. of dry dimethylformamide was heated at 145° for 6 hours. The solution was cooled to 0° and the resulting precipitate filtered and washed with cold dimethylformamide and ice water. The air dried product was then crystallized from dimethylformamide to give 5.3 g. (46%) of 1,2-dimethoxy-4,5-bis-(2,4-diamino-5-pyrimidinyl-methyl)benzene, m.p. 280°.

EXAMPLE 7

Preparation of 1,2-dimethoxy-4-(2-propenyl)-5-(2-cyano-3-methoxy-2-propenyl)benzene To a solution of 10 g. of methyl eugenol and 8.1 of 2-dimethoxymethylacrylonitrile in 200 ml. of dry methylene chloride was added 1.97 ml. of stannic chloride. After stirring for 5 hours at room temperature, 300 ml. of ether was added and the mixture washed with a 5% sodium bicarbonate solution (until basic). The organic layer was dried (MgSO₄) and the solvent removed under reduced pressure. The residue was triturated with ether to give 1,2-dimethoxy-4-(2-propenyl)-5-(2-cyano-3-methoxy-2-propenyl)benzene, m.p. 77°–79°.

EXAMPLE 8

Preparation of 2,4-diamino-5-[2-(2-propenyl)-4,5-dimethoxybenzyl]-pyrimidine

The 1,2-dimethoxy-4-(2-propenyl)-5-(2-cyano-3-methoxy-2-propenyl)benzene (15 g.) was reacted with 6.1 g. of guanidine carbonate in 40 ml. of dry dimethylformamide and heated at 145° for 6 hours. The mixture was then cooled (0°) and the precipitate filtered and washed with cold dimethylformamide and then ice water. The product was air dried and triturated with ether to give 12 g. (71%) of 2,4-diamino-5-[2-(2-propenyl)-4,5-dimethoxybenzyl]pyrimidine, m.p. 170°–171°.

EXAMPLE 9

Preparation of 2,4-diamino-5-[2-(1-propenyl)-4,5-dimethoxybenzyl]-pyrimidine

To a solution of 0.94 g. of potassium t-butoxide in 100 ml. of dry t-butanol was added 5 g. of 2,4-diamino-5-[2-(2-propenyl)-4,5-dimethoxybenzyl]pyrimidine. After refluxing overnight, the t-butanol was removed under vacuum and the residue treated with water. The resulting precipitate was filtered, air dried and then dissolved in a minimum of methylene chloride and dried (MgSO₄). The solvent was removed under vacuum to give 4.6 g. of 2,4-diamino-5-[2-(1-propenyl)-4,5-dimethoxybenzyl]pyrimidine, m.p. 204°–208°. A small sample was crystallized (methylene chloride-ether) for analysis m.p. 208°–210°.

EXAMPLE 10

| Capsule Formulation | Per capsule, mg. |
|---|---|
| N¹-(3,4-dimethyl-5-isoxazolyl)-sulfanilamide 2,4-diamino-5-[2-(2-propenyl)-4,5-dimethoxybenzyl] pyrimidine | 250 |
| Lactose | 68 |
| Corn starch | 27 |
| Talc | 5 |
| Total Weight | 375 |

Procedure:

(1) The N¹-(3,4-dimethyl-5-isoxazolyl)-sulfanilamide, 2,4-diamino-5-[2-(2-propenyl)-4,5-dimethoxybenzyl]pyrimidine, lactose and corn starch are mixed in a suitable mixer.

(2) The mixture is further blended by passing through a Comminuting Machine with a No. 1A screen with knives foward.

(3) The blended powder is returned to the mixer, the talc added and blended thoroughly. The mixture is then filled into No. 4 hard shell gelatin capsules on a capsulating machine.

EXAMPLE 11

Preparation of 1,2-dimethoxy-4-methyl-5-(2-cyano-3-methoxy-2-propenyl)benzene and 3-(4,5-dimethoxy-2-methylphenyl)-2-dimethoxypropionitrile To a solution of 10 g. of 3,4-dimethoxytoluene and 11.5 g. of α-methoxymethylene-β-methoxypropionitrile dissolved in 40 ml. of methylene chloride was added 5 g. of p-toluenesulfonic acid. The reaction mixture was refluxed for 4 hours, diluted with ether and the resulting solution washed with a 5% sodium bicarbonate solution. The combined aqueous washings were backwashed with ether and the organic layers were then combined and dried (magnesium sulfate). The solvent was removed under pressure and the residue distilled to give 14.4 g. of a mixture of 1,2-dimethoxy-4-methyl-5-(2-cyano-3-methoxy-2-propenyl)benzene and 3-(4,5-dimethoxy-2-methylphenyl)-2-dimethoxymethylpropionitrile, b.p. 175°–180°/0.03 mm.

I claim:

1. A compound of the formula

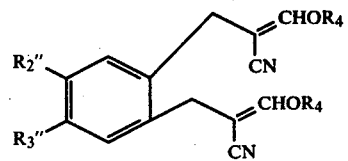

III wherein $R_2''$ and $R_3''$ are, independently, lower alkoxy, and $R_4$ is lower alkyl.

2. A compound of the formula

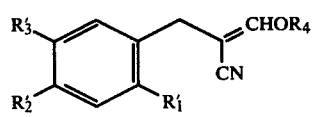

VIII wherein $R_1'$, $R_2'$ and $R_3'$ are hydrogen, lower alkyl, lower alkoxy or lower alkenyl, provided that at least one of $R_1'$, $R_2'$ and $R_3'$ is lower alkenyl, and $R_4$ is lower alkyl.

* * * * *